United States Patent [19]
Pfeffer et al.

[11] 3,963,784
[45] June 15, 1976

[54] PROCESS FOR THE PREPARATION OF ALDEHYDES

[75] Inventors: Philip E. Pfeffer, Warrington; Leonard S. Silbert, Philadelphia, both of Pa.

[73] Assignee: The United States of America as represented by the Secretary of Agriculture, Washington, D.C.

[22] Filed: Dec. 19, 1973

[21] Appl. No.: 426,159

Related U.S. Application Data

[60] Continuation-in-part of Ser. No. 203,917, Dec. 1, 1971, abandoned, which is a division of Ser. No. 853,505, Aug. 27, 1969, Pat. No. 3,652,612.

[52] U.S. Cl. ............................................. 260/601 R
[51] Int. Cl.$^2$ ........................................ C07C 45/18
[58] Field of Search ............ 260/526 R, 526 N, 413, 260/601 R

[56] References Cited
FOREIGN PATENTS OR APPLICATIONS
157,573   12/1904   Germany ........................ 260/601 R

OTHER PUBLICATIONS

Creger, "J.A.C.S.," vol. 89, pp. 2500–2501, (1967).

Patai (Ed), "The Chem. of Carboxylic Acids and Esters," Intersci., (1969), pp. 362, 593–595.

*Primary Examiner*—Raymond V. Rush
*Assistant Examiner*—D. B. Springer
*Attorney, Agent, or Firm*—M. Howard Silverstein; William E. Scott; David G. McConnell

[57] ABSTRACT

Aldehydes are prepared by metalating an aliphatic carboxylic acid with lithium diisopropylamide in a mixed solvent system of tetrahydrofuran-hexane-hexamethylphosphoramide to form a dianion of the acid, reacting the dianion in the mixed solvent system with ethyl formate and decarboxylating the resulting alpha-aldehyde acid salt.

1 Claim, No Drawings

PROCESS FOR THE PREPARATION OF ALDEHYDES

This is a continuation-in-part of application Ser. No. 203,917, filed Dec. 1, 1971, now abandoned, which is a division of application Ser. No. 853,505, filed Aug. 27, 1969, now U.S. Pat. No. 3,652,612.

This invention relates to the preparation of metalated carboxylic acids and more specifically to an improved method of preparing dianions of straight chain saturated or unsaturated aliphatic carboxylic acids. In addition, this invention relates to the preparation of α-substituted carboxylic acids and their decarboxylated derivatives.

The preparation of α-sodio sodium acetate in good yields from sodamide was first shown by DePree and Closson (J.A.C.S. 80, 2311, 1958). However, their method could only be applied to acetic acid because the α-sodio sodium salts of any of the higher homologous acids decomposed.

The preparation of lithium α-lithio isobutyrate by reacting isobutyric acid with lithium diisopropylamide in tetrahydrofuran (THF)-hexane solution and reaction of the dianion with alkyl halides has been described by P. L. Creger (J.A.C.S. 89, 2500–2501, 1967). However, the present inventors found this procedure unsatisfactory in the preparation of dianions from straight chain acids and in the subsequent alkylation of the dianions. Typically, the reaction mixtures of dianions were cloudy and heterogeneous and yields of the alkylated products were not good. For example, in the preparation of the α-butyl derivatives of heptanoic, pelargonic, myristic and stearic acids, the yields were less than 45%. Thus, a process for preparing dianions and their alkylated derivatives in high yield from long straight chain acids is highly desirable.

It is therefore an object of this invention to provide an improved method of preparing dianions of long straight chain aliphatic carboxylic acids.

Another object of this invention is to provide an improved method of preparing the α-alkyl derivatives of straight chain aliphatic carboxylic acids.

Still another object of this invention is to provide an improved method of preparing the decarboxylated derivatives of α-substituted carboxylic acids.

According to this invention the above objects are accomplished by the addition of the very polar solvent hexamethylphosphoramide (HMPA) to THF as a co-solvent for the preparation of the dianion and as the reaction medium in the preparation of the α-substituted carboxylic acids and their decarboxylated derivatives.

Other basic solvents such as dimethylsulfoxide and N,N-dimethylformamide react with the dianion and regenerate acid, thus providing no product yield. Consequently, it was totally unexpected that HMPA, a strong basic polar solvent, would not metalate or compete for base as do the other basic solvents.

The superiority of the process of the present invention is demonstrated in the preparation of the α-butyl derivatives of a number of aliphatic acids. Whereas the yields when the derivatives were prepared without the benefit of the improvement of the present invention were below 45%, the percent yields of the α-butyl derivatives of heptanoic, pelargonic, myristic and stearic acids, when prepared by the process of the present invention were 95, 95, 90 and 87, respectively. Yields of the α-butyl derivatives of oleic and undecylenic acids were greater than 90%. An important fact to note relevant to the α-butyl derivatives of the unsaturated acids is that no double bond migration occurred.

Addition of the very polar solvent HMPA not only solubilizes the dianion making the reaction homogeneous but it also has an accelerating effect on the reaction and drives it to near completion. This beneficial effect was surprising and totally unexpected in view of the fact that other basic polar solvents had a detrimental effect on the reaction.

In addition to being a superior method of converting carboxylic acids into their α-lithio lithium salts (dianions) and then to the α-alkyl derivatives, the process of the present invention is also a novel way of preparing alkyl nitro compounds, substituted malonic acids, α-hydro compounds, dithio-alkeneacetals and aldehydes.

Although the conventional form of expressing the preparation and reaction of dianions as used in this specification may make them appear to be monovalent anions, the products prepared by the method of this invention are truly dianions. The fact that the term dianion is correct is documented in J. Org. Chem. 36, 3290-3293,1971. Although substitution of the dianions described in the J. Org. Chem. article occurs at the α-position, the substitution occurs through the double bond system as in any enolate anion. For example, the configuration is

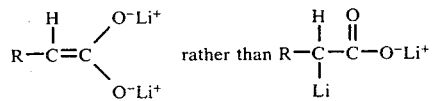

Thus, one may write the metal in the α-position on the carbon for conventional purposes since this is the point at which the hydrogen is initially removed. However, the stable structure is dianionic with the two Li metal atoms attached to oxygen. Further documentation is found in the work of Kuo et al., Chem. Commun. 136, 1971, which confirms that the structure of applicants compounds is dianionic by trapping the dianion intermediate with $(CH_3)_3LiCl$. Thus, Kuo et al. obtained

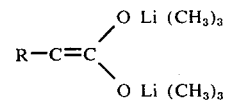

which confirms the intermediacy of

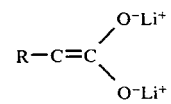

In addition, Ivanoff (Naturwissenschaften 51, 286, 1964, demonstrated that organo metallic derivatives of acetylenic carboxylic acid are also dianionic in nature.

A typical procedure for the preparation of the dianion is as follows: Into a dry, nitrogen flushed flask under a nitrogen atmosphere was added 35 ml. of anhydrous tetrahydrofuran (THF) and 4.9g (0.049m) of diisopropylamine. To the magnetically stirred solution 30 ml. of 1.6m (0.048m) n-butyl lithium in hexane was added at such a rate as to maintain the reaction temperature below 0°C. n-Heptanoic acid (2.95g; 0.0227m) was then added to the cold basic solution and again the temperature was kept below 0°C. After stirring for an additional 15 minutes, 9ml (0.050m) of hexamethylphosphoramide (HMPA was added and the solution which had been milky white became transparent and light yellow. The molar ratio of this mixed solvent system, that is, the molar ratio of HMPA to THF is not critical. The HMPA solubilizes the reaction mixture and its concentration relative to that of THF is not critical to the success of the reaction. However, as used in this typical procedure, the preferred ratio is about 2 to 1.

Dianions of other straight chain saturated and unsaturated aliphatic carboxylic acids were made by substituting in the place of n-heptanoic acid a 0.227 molar amount of the appropriate acid.

At this point an electron deficient species may be added at once to the dianion at 0°C. to give the corresponding α-substituted carboxylates or decarboxylated products.

PREPARATION OF ALDEHYDES

The dianion having the appropriate straight chain saturated or unsaturated aliphatic alkyl radical was prepared as previously described. The dianion was transferred to an addition funnel and then slowly over a period of about an hour added to a solution of ethyl formate (0.049 mole) in 15 ml. of anhydrous THF while the reaction mixture was kept at about −5° to 0°C. The reaction mixture was stirred for about 1.5 hrs., then heated at about 55°C. for 30 minutes to effect decarboxylation and then acidified with 10% HCl to neutralize and isolate the product. Water was added to destroy any excess base and the reaction mixture was then extracted with pentane. The pentane extracts were combined and extracted with 10% HCl, 10% sodium carbonate solution, water and saturated sodium chloride solution. The pentane solution was dried and then the solvent was removed. Pure heptanal and pure nonanal were obtained in yields of greater than 70% by this process. The unsaturated aldehyde, cis-9-octadecenal was also prepared in good yield. Reaction of the dianion with ethyl formate and subsequent decarboxylation to obtain long chain aldehydes is shown in the following equation:

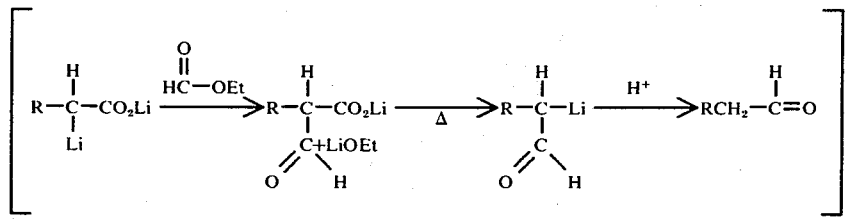

The α-substituted carboxylic acids and their decarboxylated derivatives prepared by the process of this invention are useful in many areas of commercial endeavor such as in the preparation of hypnotics, deodorants, fumigants, photography, polymers, rubber, tobacco flavorants, waterproofing, perfumes, food flavorings and as chelating agents.

We claim:

1. A direct process for the preparation of aldehydes, comprising the steps of:
  a. metalating with lithium diisopropylamide in a mixed solvent system of tetrahydrofuranhexane-hexamethylphosphoramide at a temperature below 0°C., a carboxylic acid selected from the group consisting of unsubstituted straight chain saturated and olefinically unsaturated straight chain hydrocarbyl carboxylic acids having from 7 to 18 carbon atoms, the point of unsaturation of said unsaturated acids being at least four carbon atoms from the carboxylic acid function, to form a dianion of said carboxylic acid;
  b. reacting said dianion in the aforesaid mixed solvent system with ethyl formate at a temperature of from about −5° to 0°C. to form an alpha-aldehyde salt and lithium ethoxide;
  c. warming the alpha-aldehyde acid salt in the mixed solvent system to a temperature below 55°C. to effect decarboxylation; and
  d. acidifying with a dilute acid solution the product of step (c) to obtain a free aldehyde in slightly acidic media.

* * * * *